(12) United States Patent
Förster (10) Patent No.: US 7,785,101 B2
(45) Date of Patent: Aug. 31, 2010

(54) SELF-LIGATING BRACKET FOR USE IN ORTHODONTICS

(76) Inventor: Rolf Förster, Vogesenallee 58, Pforzheim (DE) D-75173

( * ) Notice: Subject to any disclaimer, the term of this patent is extended or adjusted under 35 U.S.C. 154(b) by 86 days.

(21) Appl. No.: 11/983,305

(22) Filed: Nov. 8, 2007

(65) Prior Publication Data

US 2008/0113311 A1     May 15, 2008

(30) Foreign Application Priority Data

Nov. 11, 2006   (DE) .................. 10 2006 053 215

(51) Int. Cl.
*A61C 7/30*     (2006.01)
(52) U.S. Cl. ........................................ 433/11
(58) Field of Classification Search ............... 433/8–17
See application file for complete search history.

(56) References Cited

U.S. PATENT DOCUMENTS

| | | | |
|---|---|---|---|
| 5,322,435 A | 6/1994 | Pletcher | |
| 5,466,151 A | 11/1995 | Damon | |
| 5,613,850 A | 3/1997 | Wildman et al. | |
| 5,857,850 A * | 1/1999 | Voudouris | 433/11 |
| 5,913,680 A * | 6/1999 | Voudouris | 433/10 |
| 5,971,753 A * | 10/1999 | Heiser | 433/11 |
| 6,071,118 A | 6/2000 | Damon | |
| 6,939,133 B2 * | 9/2005 | Voudouris | 433/11 |
| 7,267,545 B2 | 9/2007 | Oda | |
| 2007/0248928 A1 * | 10/2007 | Damon | 433/10 |

FOREIGN PATENT DOCUMENTS

| | | |
|---|---|---|
| EP | 1 679 048 A2 | 7/2006 |
| WO | WO 99/40871 | 8/1999 |

* cited by examiner

*Primary Examiner*—Cris L Rodriguez
*Assistant Examiner*—Michael R Ballinger

(57) ABSTRACT

A self-ligating bracket for use in orthodontics includes a bracket also closeable by a slide which is undetachably held in both a closed position and in an open position. The slide is easy to open and to close, which gives the bracket an acceptably attractive appearance and which provides little risk of food residues getting trapped that are difficult to remove.

23 Claims, 4 Drawing Sheets

SELF-LIGATING BRACKET FOR USE IN ORTHODONTICS

The present invention relates to a self-ligating bracket for use in orthodontics which comprises a base, an occlusal wall extending from the base and having at least one occlusal ligature wing, a gingival wall extending from the base and having at least one gingival ligature wing, a slot separating the occlusal wall and the gingival wall one from the other and extending continuously in the mesial-to-distal direction, and a slide which is retained in a guide provided in the occlusal wall and/or in the gingival wall and which is arranged for being displaced in the guide in the gingival-to-occlusal direction, between a closed position in which the slide bridges the slot and an open position in which the slot is open in the labial direction; and means capable of retaining the slide in both its closed position and in its open position. A bracket of that kind has been known from U.S. Pat. No. 5,322,435 A. For closing its slot, the known bracket comprises a slide arranged for being displaced in lateral guide grooves provided in both the occlusal wall and the gingival wall of the bracket. In order to be able to retain the slide in both its open position and its closed position, a bore opening toward the slide is provided in one of the walls of the bracket which bore contains either a helical spring acting on the bottom of the slide or a cylindrical bolt made from an elastomeric plastic material, that projects beyond the opening of the bore and which acts upon the bottom of the slide. Two recesses are provided in the bottom of the slide. One of the recesses is engaged by the spring or by the end of the bolt which projects from the bore in the open position of the slide. The other recess is engaged by the spring or by the end of the bolt which projects from the bore in the closed position of the slide. A projection, separating the two recesses, has to overcome the helical spring or the bolt, respectively, when the slide is to be displaced between its open position and its closed position. Overcoming the two elements is difficult because the slide is displaced at a right angle relative to the direction in which the spring has to be urged back into the bore. Further, there is a risk that the spring and the slide may get mechanically stuck one relative to the other or that the spring may be damaged. The elastomeric plastic bolt cannot be urged back into the bore, the plastic material being non-compressible in its solid condition. Instead, the slide must be bent to move it over the plastic bolt. This requires that the slide be made correspondingly thin in order to keep the force necessary to displace the bolt within practicable limits. In view of the small dimensions brackets normally have the known bracket is difficult to realize.

U.S. Pat. No. 5,613,850 A describes a self-ligating bracket where the slide is combined with a U-shaped spring that encloses the slide. One of the two legs of the spring is provided with a projection, produced by punching, so that the projection snaps into a recess in a wing of the bracket in the closed position. When that leg is pressed down, the spring can be moved out of its locked position and the slide can be pushed out of its closed position. The slide is not secured in the open position so that it may get lost, which may have especially disagreeable consequences when it happens in a person's mouth because then there is a risk that the slide may be swallowed.

EP 1 697 048 A2 discloses a self-ligating bracket where the slide is retained in its closed position by a spring which is seated in a hole in the bracket body and is provided with a projecting leg that is bent off twice for engaging a passage opening in the slide. The spring can be pushed out of the hole, and the slide can be removed from the bracket. The spring is not capable of retaining the slide in the open position. It is a further disadvantage of that solution that saliva residues may accumulate in the hole of the slide and beneath the slide that cannot be removed neither by means of a toothbrush nor by mouth rinses.

EP 1 679 048 A2 further describes a self-ligating bracket the slide of which is provided with an oblong hole passed by a locking pin which is anchored in a bore in the bracket once the slide has been seated in the bracket. The play available to the locking pin in the oblong hole defines the distance the slide can be displaced in the bracket between the closed position and the open position. Once the locking pin has been fitted, the slide no longer can be removed. The locking pin as such is not in a position to retain the slide in the closed position or in the open position. A certain blocking effect can be achieved for the slide by friction only, although this is not sufficient to retain the slide reliably in either the closed position or the open position.

SUMMARY OF THE INVENTION

Now, it is the object of the present invention to provide a self-ligating bracket for use in orthodontics where the slot of the bracket can be closed by a slide which as such need not be resilient, which may have a mechanically stable design, which is undetachably held in both the closed position and in the open position, which is easy to open and to close, which gives the bracket an acceptably attractive appearance and which provides little risk of food residues getting trapped that are difficult to remove.

That object is achieved by a self-ligating bracket for use in orthodontics which comprises a base, an occlusal wall extending from the base and having at least one occlusal ligature wing, a gingival wall extending from the base and having at least one gingival ligature wing, a slot separating the occlusal wall and the gingival wall one from the other and extending continuously in the mesial-to-distal direction, and a slide which is retained in a guide provided in the occlusal wall and/or in the gingival wall and which is arranged for being displaced in the guide in the gingival-to-occlusal direction, between a closed position in which the slide bridges the slot and an open position in which the slot is open in the labial direction; and means capable of retaining the slide in both its closed position and in its open position. At least one recess is provided in which a spring is seated, the at least one recess is arranged in the gingival wall or in the occlusal wall of the bracket and is provided with an opening which faces the slide and from which a spring projects toward the outside, a first stop is provided on the slide that abuts against the at least one spring in the open position of the slide, a projection is provided on that side of the slide, which faces the at least one spring, and which is arranged in such a way that during displacement of the slide to its closed position, it will come to abut against the at least one spring before it reaches its closed position, sufficient space is available on both sides of the projection for accommodating the end of the at least one spring that projects from the recess, the at least one recess for the at least one spring expands toward its opening facing the slide so that the spring is given sufficient play in the recess for bending of the spring in the two possible directions of displacement of the slide, a second stop is provided on the bracket, for abutment of the slide in its closed position, once its projection has overcome the at least one spring.

A second solution to the object, based on the same inventive idea, is achieved by a self-ligating bracket for use in orthodontics which comprises a base, an occlusal wall extending from the base and having at least one occlusal ligature wing, a gingival wall extending from the base and having at least one gingival ligature wing, a slot separating the occlusal wall and the gingival wall one from the other and extending continuously in the mesial-to-distal direction, and a slide which is retained in a guide provided in the occlusal wall and/or in the gingival wall and which is arranged for being displaced in the guide in the gingival-to-occlusal direction, between a closed position in which the slide bridges the slot and an open position in which the slot is open in the labial direction, and means capable of retaining the slide in both its closed position and in its open position. There are provided at least one first spring and at least one second spring, each of which is seated in a recess and provided with an opening facing the slide, with the respective spring projecting from the respective opening, the at least one recess for the at least one first spring is provided in the first wall of the bracket, the at least one recess for the at least one second spring is provided in the second wall of the bracket, a first stop is provided on the slide that abuts against the at least one spring in the open position of the slide and that abuts against the at least one second spring in the closed position of the slide, the at least one recess for the at least one spring expands toward its opening so that the first spring is given sufficient play in its recess for bending of the first spring in the closing direction of the slide, the at least one recess for the at least one spring expands toward its opening so that the second spring is given sufficient play in its recess for bending of the second spring in the two possible directions of displacement of the slide, the space available in the at least one recess for the at least one spring is configured and sized so that, when being introduced into the guide for the first time, the slide will urge the at least one first spring into the expanded portion of the recess, by bending of the at least one first spring, until the first stop of the slide is capable of overcoming the at least one first spring, the space available in the at least one recess for the at least one second spring, for bending of the respective second spring, is configured and sized so that first stop of the slide is capable of overcoming the at least one second spring in both possible directions of displacement by bending of the at least one second spring, a second stop is provided on the bracket, against which the slide will abut in its closed position once it has overcome the at least one second spring.

Advantageous further developments of the invention are the subject-matter of the sub-claims.

In the bracket according to the invention the means for retaining the slide in both its closed and its open position comprise at least one recess arranged in the gingival wall or in the occlusal wall of the bracket and provided with an opening which faces the slide and from which a spring, located in the recess, projects toward the outside. In the present context, the term spring is used to describe any element that reacts to deformation by a restoring force which tends to restore the element to its non-deformed shape. The spring should be flexible so that it can be deflected by a stop provided at the bottom of the slide when the stop of the slide hits upon the spring. The term bottom of the slide is meant in this connection to describe that side of the slide that faces the base of the bracket. A first stop provided on the slide abuts against the at least one spring in the open position of the slide whereby the slide is hindered to slip off its guide in full; instead, the slide remains undetachably connected with the bracket in its open position.

Further, a projection is provided at the bottom of the slide. The arrangement of that projection is such that during displacement of the slide to its closed position it will come to abut against the at least one spring before it reaches its closed position. As displacement of the slide continues, until it reaches the closed position, the projection can overcome the end of the spring, that projects from the recess, by deflecting the spring in the direction of movement of the slide. In order to permit this action to take place, the recess accommodating the spring expands toward its opening facing the slide so that the spring is given sufficient play for being bent during displacement of the slide to its closed position and also during displacement of the slide to its open position. Such bending of the spring has the effect to reduce the amount by which the spring projects from the recess. As a result, the projection at the bottom of the slide is permitted to overcome the spring without thereby subjecting the slide to any bending stresses.

Once the projection of the slide has overcome the spring during displacement of the slide to its closed position, the spring should spring back and resume its original shape. This is rendered possible by providing sufficient space on both sides of the projection, i.e. on both the forward and the rear sides of the projection, related to the direction of displacement of the slide, for accommodating the spring end projecting from the recess even when no restoring force is produced by the spring. The space in which the projecting end of the spring is accommodated when the slide occupies its closed position need not be larger, or at least not substantially larger, than the projecting end of the spring so that the position of the slide in the closed position is secured by the spring free from play or with little play. Alternatively, the space which accommodates the projecting end of the spring when the slide occupies its closed position may be larger than the extension of the spring in the direction of movement of the slide provided the slide comes to abut against a second stop on the bracket body in its closed position.

The invention provides substantial advantages:

- A spring which due to its particular kind and way of installation can be deflected and subjected to bending stresses by the slide during displacement of the latter, allows the spring to be overcome by mere application of a defined force which is determined by the restoring force of the spring produced during bending of the spring.
- When transferring the slide from its open position to its closed position the spring force has to be overcome only when the projection provided at the bottom of the slide abuts against the spring to overcome the latter by deflection. As long as the spring is not deflected no spring force has to be overcome for the spring to apply itself to, and to exert pressure on, the bottom of the slide; instead, the spring may maintain a certain spacing from the slide.
- Up to the moment the projection of the slide hits upon and deflects the spring, the slide can be moved easily and without much force. The force required will rise only shortly before the closed position is reached, and finally a clearly noticeable locking action will occur indicating that the slide is secured in its closed position.
- During first insertion of the slide in its guide, the spring is overcome by deflection and the slide initially assumes its open position in which it is secured against slipping off by the first stop which is provided at the bottom of the slide and which overcomes the spring when the slide is inserted for the first time.
- As the slide does not have to be subjected to bending stresses during displacement between its open position and its closed position, it may be given a flexurally stiff design. This is an advantage with respect to absorption of forces that are exerted on the bottom of the slide by an arch wire arranged in the slot of the bracket.
- There is no need for a passage opening in the bracket or its slide, that would be difficult to clean.
- For operation of the slide, an easy-to-clean indentation may be provided in the upper surface of the slide. The attending orthodontist can then engage that indentation by a tool. Generally, the upper surface of the slide may have a plain design and may be aligned with the upper surface of the adjacent ligature wings which not only facilitates the necessary cleaning work but also gives the bracket an attractive appearance without impairing the technical function of the bracket.

The invention is suited for brackets that may consist of any materials known for brackets, i.e. for brackets and slides made from metal, ceramics or plastic materials.

The recess that accommodates the spring may be equally expanded in both directions of the slide. Preferably, however, the recess has an asymmetrical design in that the bending play provided for the spring by the expansion of the recess is suitably configured and sized so that when the spring is bent in the direction of the first stop the amount by which the end of the spring projects from the recess can be reduced to a smaller amount than when it is bent in the opposite direction. This has the result that as the slide is inserted into the guide and is then transferred to its closed position, the spring can be overcome more easily than when the slide is moved in the opposite direction. This creates the condition that the bracket can be closed more easily than opened. This is an advantage and desirable and has the effect that once the slide has been fitted it cannot practically get lost any more, and this is an advantage and desirable as well.

Preferably, the at least one spring is located in the first wall of the bracket. The term first wall of the bracket is understood to describe that wall where the slide is introduced into its guide. The second stop, against which the slide abuts in its closed position, is preferably formed on the second wall of the bracket and is preferably arranged so that the forward end of the slide abuts against the second stop. The term forward end of the slide is meant to describe that end which is the leading end when the slide is moved to its closed position.

Preferably, the at least one spring is provided in the gingival wall of the bracket, whereas the second stop is provided on the occlusal wall so that the slide is moved from its open position to its closed position starting out from the gingiva. However, the at least one spring may also be arranged in the occlusal wall, in which case the second stop would be arranged on the gingival wall, so that the slide would be transferred to its closed position in the occlusal-to-gingival direction. That variant provides especially high safety from the slide being opened by the biting action.

The bracket according to the invention needs a single spring, only, which preferably is arranged centrally, related to the length of the bracket. The length of the bracket is measured in the longitudinal direction of the slot.

A bracket where a spring is provided in both the gingival wall and the occlusal wall of the bracket is the subject-matter of independent claim 6. In that case, one of the springs, preferably the spring in the gingival wall, serves to secure the slide from getting lost in its open position, whereas the other spring, preferably the spring in the occlusal wall, serves to secure the slide in its closed position. Each of the springs is seated in a recess that expands in the direction of the slide, over the region adjacent the slide. It is sufficient in this connection if the spring, which secures the slide from getting lost, can be deflected merely in the closing direction of the slide so that the recess for the first spring needs to expand only in that one direction. The slide then can be introduced into its guide easily, but cannot be removed any more, or can at best be removed by application of a particularly high force that would provide a risk of damage for the spring. Normally, once the slide has been introduced into its guide, it does not need to be removed from the bracket later.

The second spring, intended to secure the slide in its closed position, can be deflected in both directions during displacement to its closed position and also during displacement to its open position, because the spring has to be overcome by a projection or stop during both operations, the closing and the opening operation. Correspondingly, the recess for the second spring expands in both directions, either symmetrically or asymmetrically.

In the embodiment of the bracket according to claim 6, a stop must be provided only at the bottom of the slide for abutment of the second spring in the closed position of the slide. Starting out from that stop, a flat, preferably cuboid recess is needed for displacement of the slide between its closed position and its open position, which stop can be engaged by the projecting ends of the two springs and which extends, in the direction of displacement, at least over a length that permits the two springs to engage that flat recess of the slide in the closed position of the slide. Accordingly, the length of the flat recess at the bottom of the slide, measured in the direction of displacement, is at least equal to the spacing of the two springs, measured over the sides of their projecting ends that face away one from the other.

There is no need for an intermediate projection at the bottom of the slide in the case of that variant of the invention.

The advantages claimed for the bracket according to claim 1 apply correspondingly to the bracket according to claim 6.

The embodiment according to claim 1 need not necessarily comprise a single spring, only, in the occlusal wall of the bracket, but may also have a plurality of springs arranged one beside the other, conveniently in separate recesses. Such an arrangement may increase the functional safety of the bracket. The same applies correspondingly to the variant of the invention according to claim 6: In that case, a plurality of springs may be arranged one beside the other in the gingival wall and/or in the occlusal wall of the bracket.

Preferably, however, the bracket is configured so that a single spring, preferably designed as a leaf spring, is provided in the gingival wall and/or the occlusal wall. Alternatively, the springs may have a rod-shaped configuration. Rod-shaped springs are advisable mainly in cases where a plurality of springs are to be arranged one beside the other. Further, a spring of comb-like structure, fitted in a slot-shaped recess so that the ends of the teeth of the comb project beyond the end of the recess, is likewise possible.

In both variants of the invention, the opening of the at least one recess points away from the base of the bracket, and the at least one recess is oriented in such a way that it extends into the gingival wall or the occlusal wall, respectively, of the bracket in perpendicular or nearly perpendicular direction relative to the slide.

Preferably, the slide is a predominantly flat structure, received in straight guides. Alternatively, however, it is also possible to give the guides the form of a circular arc and to introduce a correspondingly curved slide into those guides.

The springs may be fixed in the recess in which they are received for example by an adhesive. Alternatively, the springs may be simply fitted in their respective recess, without fixing them by means of an adhesive, the springs being secured by the slide at least in the closed position of the slide. In order to secure the springs from getting lost in the merely temporary open position of the slide it will be sufficient to retain them in their recess by friction, for example by sort of a press fit.

The springs may be made from metal in full or in part, or may be made from a plastic material having an elastic or elastomeric modulus of resilience, especially from polyoximethylene, a material that offers sufficient strength and an adequate modulus of resilience, combined with adequate durability at the conditions prevailing in a person's mouth.

The bracket and its slide preferably consist of a ceramic material, the bracket preferably consisting of aluminum oxide, the slide preferably consisting of a ceramic material having a strength higher than aluminum oxide, especially of zirconium oxide.

The one spring or the plurality of springs provided in the bracket are preferably beveled at their projecting end so that the beveled surface points to the opening direction of the slide. This provides the advantage that the slide can be moved over a spring more easily in the closing direction than in the opening direction.

BRIEF DESCRIPTION OF THE DRAWINGS

Further features and advantages of the invention will be described hereafter with reference to two embodiments that are illustrated in the attached drawings. Identical parts, or parts corresponding one to the other, are indicated in both embodiments by the same reference numerals.

DETAILED DESCRIPTION

Figure 1:
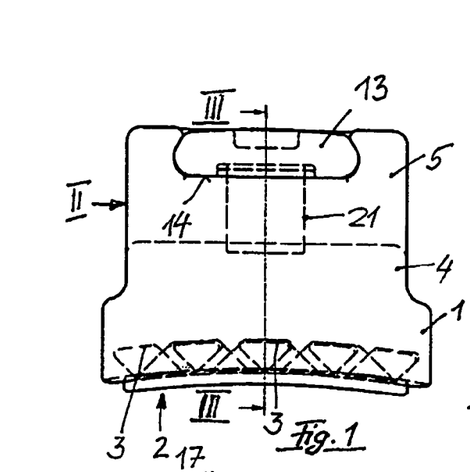
FIG. 1 shows a view of the gingival side of a bracket provided with a single spring only, with the slide in its open position.

The bracket illustrated in FIGS. 1 to 12 has a curved base 1 the curvature of which is approximated to the front of a tooth. The bottom surface 2 of the base 1, forming the lingual side of the bracket, is provided with recesses 3 of undercut shape, arranged in a row. The recesses 3 have a rectangular contour, in the cross-section shown in FIG. 3. In a cross-section normal to that cross-section, the recesses 3 have a rhombic contour, as illustrated in FIG. 1. In order to glue the bracket onto a front of a tooth, an adhesive may be applied on the bottom surface 2. The interaction between the undercut recesses 3 and the adhesive provides good bonding strength. The recesses 3 and, together with them, the undercuts are orientated identically in each row. Between the rows they are, however, alternately oriented in one and the other direction. This has the effect that when thrust is applied on the bracket in the mesial-to distal direction the same bonding strength will be achieved as in the case of thrust acting in the distal-to-mesial direction while the bonding strength is high, irrespective of the direction in which the thrust acts, when thrust in applied in the occlusal-to-gingival or the gingival-to-occlusal directions.

Figure 11:
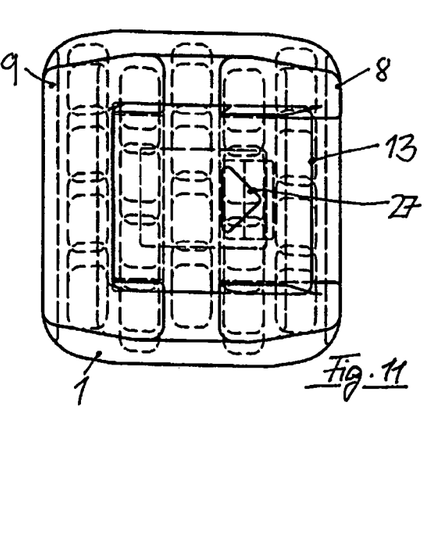
Figure 12:
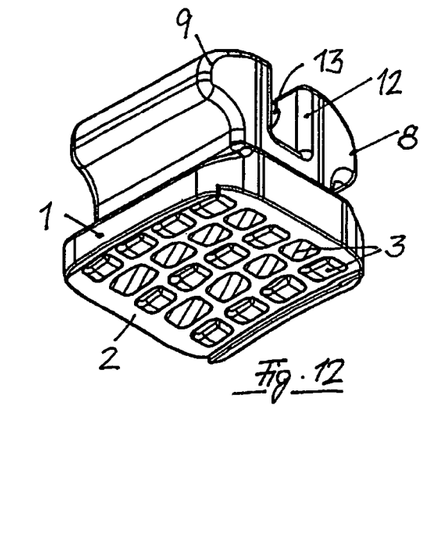
Figure 13:
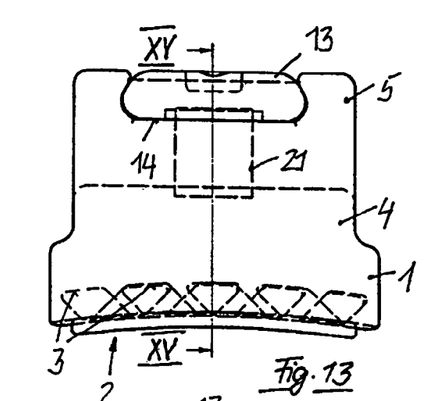
FIGS. 13 to 18 show a representation corresponding to FIGS. 1 to 6 of a bracket comprising two springs, with the slide in its open position.
Figure 14:
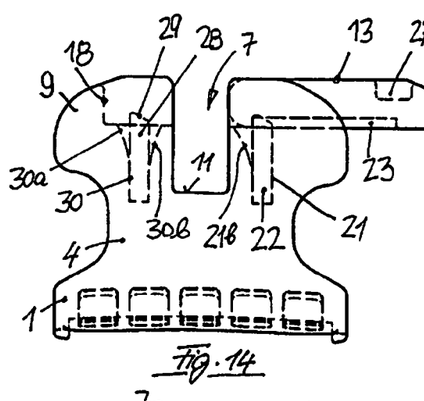
Figure 15:
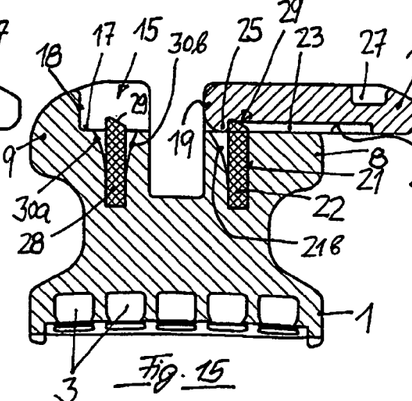
Figure 16:
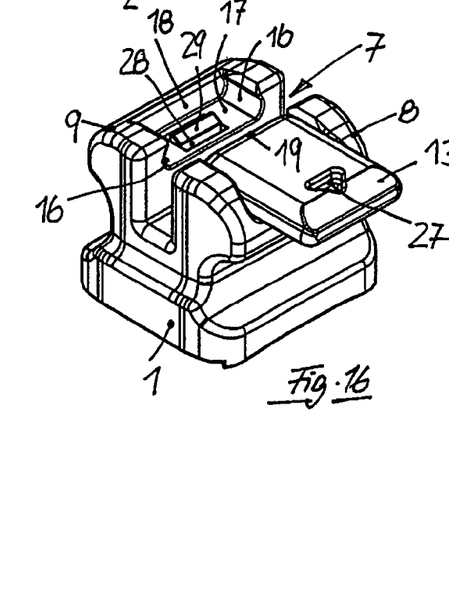
Figure 17:
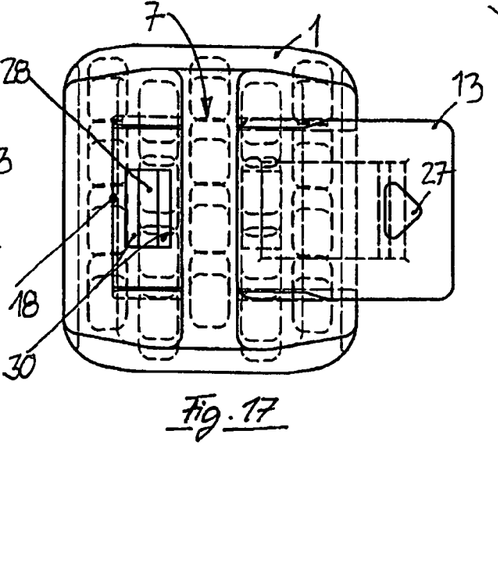
Figure 18:
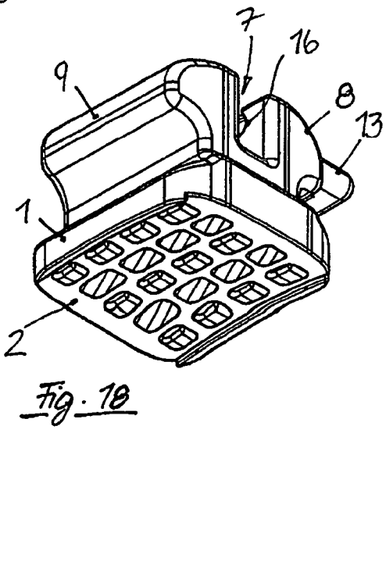
Figure 19:
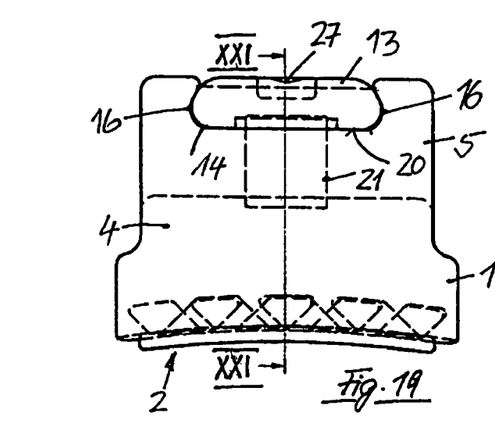
FIGS. 19 to 24 show views similar to FIGS. 13 to 18 of the bracket comprising two springs, but with the slide in its closed position.
Figure 20:
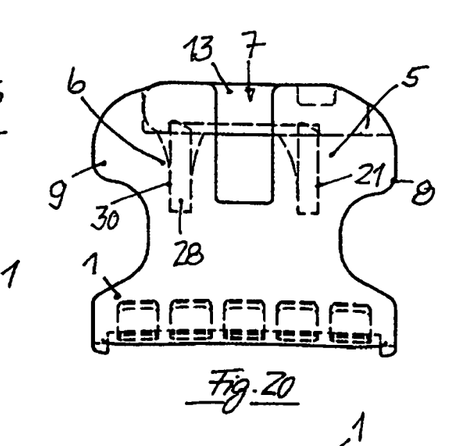
Figure 21:
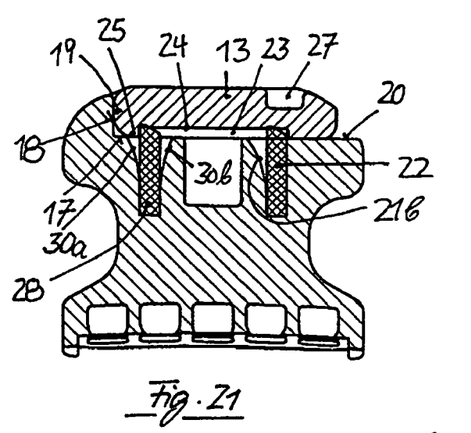
Figure 22:
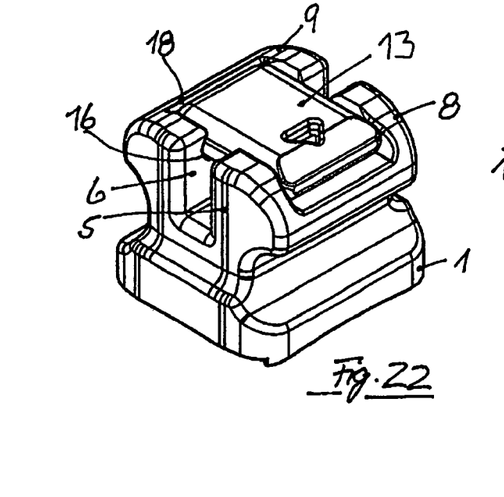
Figure 23:
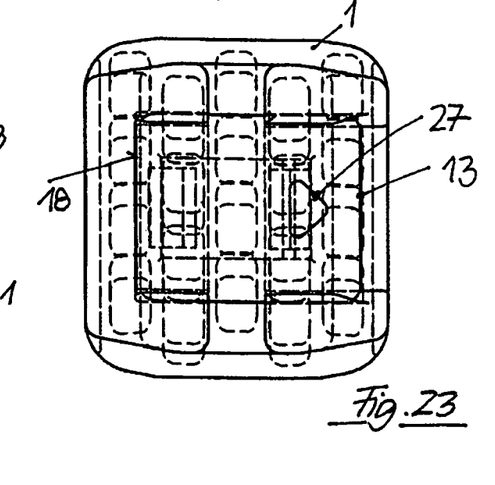
Figure 24:
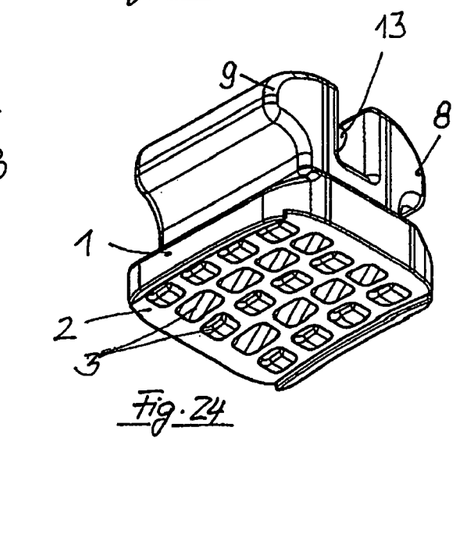

FIG. 11 shows the orientation on a tooth envisaged for a bracket with respect to the gingival-to-occlusal and the distal-to-mesial directions.

The base 1 transitions to a support 4 which carries a gingival wall 5 and an occlusal wall 6. The two walls 5 and 6 extend in parallel one to the other and are separated by a groove 7 which extends continuously along a straight line from distal to mesial and which is open in the labial direction.

A ligature wing 8, projecting in the gingival direction, is provided on the gingival wall 5. A ligature wing 9, projecting in the occlusal direction, is provided on the occlusal wall 6. These wings serve for attaching ligature wires in a manner known to the man of the art. Alternatively, the ligature wings 8 and 9 may be subdivided into pairs of ligature wings.

Figures 4, 5:
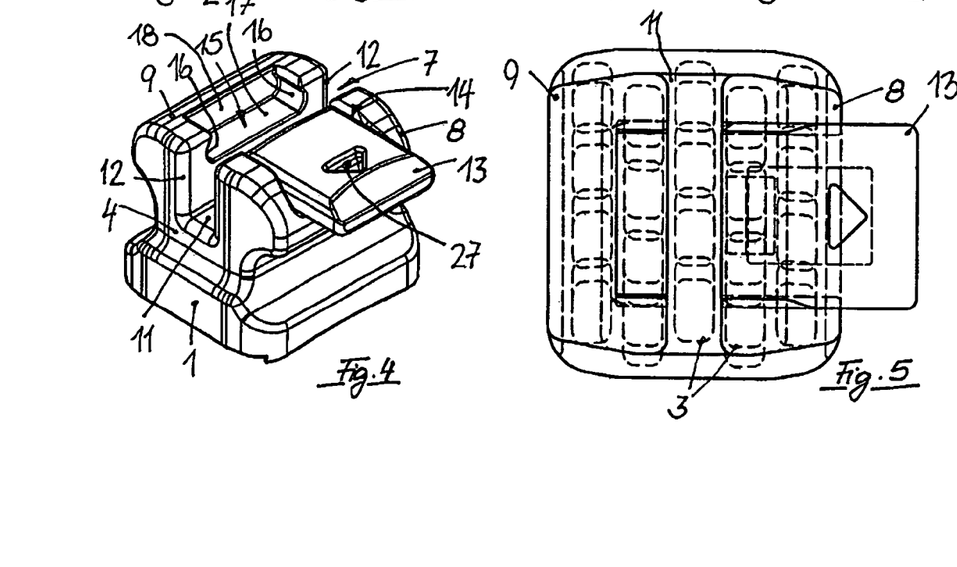
FIG. 4 shows an oblique top view of the bracket with its slide in the open position.
FIG. 5 shows a top view of the bracket.
Figure 6:
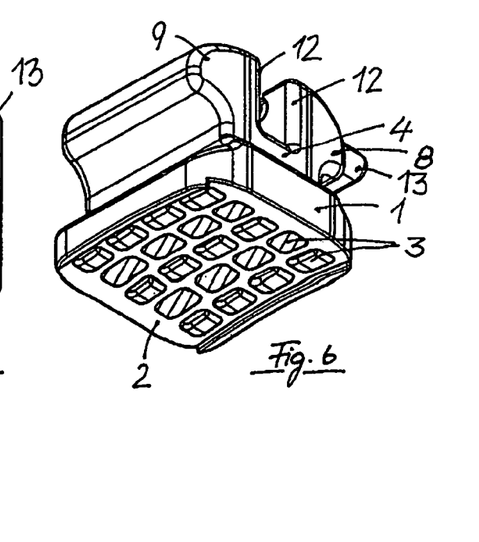
FIG. 6 shows an oblique bottom view of the bracket.
Figure 7:
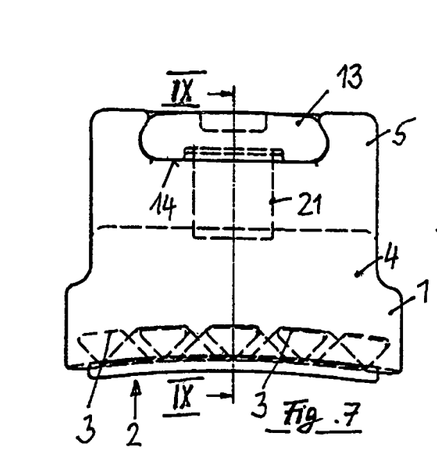
FIGS. 7 to 12 show views of the bracket similar to FIGS. 1 to 6, but with the slide in its closed position.

The groove 7, also described as slot, serves to receive an arch wire 10 which, specifically, has a rectangular cross-section, but which is not part of the bracket and, therefore, is indicated in FIG. 4 only by its contour shown in broken lines. By tensioning the arch wire 10, a pressure can be applied on the bottom 11 of the groove 7 and a torque can be applied on the walls 5 and 6 of the bracket. To this end, the clear cross-section of the groove 7 has a substantially rectangular shape. In the present case, it is delimited by the base 11 of the slot 7 and by the gingival wall 5 and the occlusal wall 6. At the ends of the slot 7, the edges 12 of the slot are rounded. In addition, at least those edges of a slide 13, that delimit the slot 7 toward the top, are rounded as well. This serves to reduce friction acting on the arch wire 10 in the slot 7, and is of advantage especially in the case of heavy misalignments of the teeth, where the arch wire 10 normally assumes an especially irregular shape.

A labial recess 14 in the gingival wall 5, and a labial recess 15 in the occlusal wall 6 accommodate a slide 13, which has a predominantly flat shape and a rectangular shape in horizontal projection. The recesses 14 and 15 are provided with undercuts 16, extending in parallel one to the other and also in parallel to the base 11 of the slot 7, which in combination with the base 17 of the recess 15 and the base 20 of the recess 14 form a coulisse for the slide 13 from which the slide 13 cannot escape in the labial direction, such movement being prevented by the undercuts 16. The recesses 14 and 15 are arranged in alignment one to the other. The recess 14 passes through the gingival wall 5, while the recess 15 in the occlusal wall 6 ends at a stop 18, i.e. the "second" stop mentioned in the claims.

Figures 2, 3, 3A:
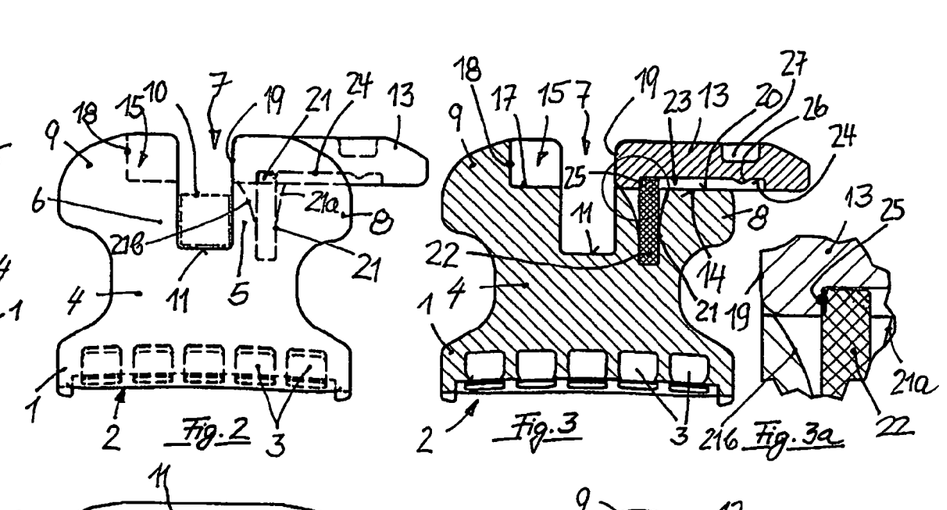
FIG. 2 shows side view II of the bracket illustrated in FIG. 1.
FIG. 3 shows cross-section III-III of the bracket illustrated in FIG. 1.
FIG. 3a shows an enlarged detail from FIG. 3.

The slide 13 can be displaced in the guide 15 to 17 in the gingival-to-occlusal direction between an open position illustrated in FIGS. 1 to 6 and a closed position illustrated in FIGS. 7 to 12. In the open position, the slot 17 is open over its full width, viewed from the labial direction. The forward end 19 of the slide 13 preferably terminates by a surface of the gingival wall 5 which delimits the slot 7, as illustrated in FIGS. 2, 3 and 5. In the closed position, the forward end 19 of the slide 13 abuts against the second stop 18 on the occlusal wall 6, a condition which is illustrated particularly clearly in FIG. 9. In the closed position, the slide 13 bridges the slot 7 so that an arch wire 10, extending in the slot, is prevented from escaping from the slot 7 in labial direction.

The gingival wall 5 comprises a slot-shaped recess 21 that starts out from the base 20 of the recess 14 and extends mainly in parallel to that surface of the wall 5 which delimits the slot 7. Oppositely arranged surfaces 21a and 21b, extending in the direction of the slot 7, extend in parallel one to the other in the lower area of the slot-shaped recess 21 and along a curved line in the upper area of the recess 21 so that the slot-shaped recess 21 expands toward the top. The curved shape of the surfaces 21a and 21b begins at approximately half the height of the slot-shaped recess 21. The surface 21b adjacent the slot 7 is curved more sharply than the other surface 21a so that an asymmetrical cross-section is obtained for the slot-shaped recess 21, as illustrated in FIG. 3. This has the result that a leaf spring 22 in cuboid form, seated in the slot-shaped recess 21, is spaced from the surface 21b a greater distance than from the surface 21a in the upper area of the slot-shaped recess 21.

So long as no restoring force occurs in the spring 22, the spring has a cuboid shape. The dimensions of the spring 22 and of the slot-shaped recess 21 are adapted one to the other so that, when fully seated in the slot-shaped recess 21, the spring 22 projects beyond the base 20 of the recess 14, as illustrated in FIG. 3. The thickness of the spring 22 is adjusted to the clear width of the slot-shaped recess 21 so that the spring 22 is retained by friction in the lower portion of the slot-shaped recess 21.

The projecting end of the spring 22 engages a recess 23 provided in the bottom of the slide 13. The depth of the recess 23 is selected to ensure that a small gap remains between the base 24 of the recess 23 and the projecting end of the spring 22, as illustrated in FIG. 3a. Generally, the recess 23 has a rectangular shape in horizontal projection. This results in a stop 25 that is in contact with the spring 22 when the slide 13 is in its open position, see FIGS. 3 and 3a. The slide 25 is the "first" stop mentioned in the claims. It prevents the slide 13 from slipping off the bracket unintentionally in its open position. Although the slide 13 can be pulled out a further length, in which case the stop 25 will urge the spring 22 against the surface 21a, with the result that the amount by which the spring 22 projects beyond the base 20 of the recess 14 will be reduced; however, such reduction will not be sufficient to allow the slide 13 to be pulled over the spring 22.

As the slide 13 is introduced into the guide 14 to 17 of the bracket for the first time, its forward end 19 hits upon the spring 22, urging it against the more sharply curved surface 21b, which is sufficient for the slide 13 to overcome the spring 22 by its stop 25.

In order to secure an arch wire 10 inserted in the slot 7, the slide 13 is transferred to its closed position, illustrated in FIGS. 7 to 12, in which the forward end 19 of the slide 13 abuts against the stop 18 on the occlusal wall 6. In order to permit the slide 13 to be retained in its closed position, there is provided, in the recess 23 at the bottom of the slide 13, a projection 26 of wedge-shaped configuration, with an angle of more than 90° between its two surfaces. The projection 26 extends in parallel to the slot 7 and to the spring 22. Its height, measured from the base 24 of the recess 23, is smaller than the depth of the recess 23.

Figures 8, 9, 9A:
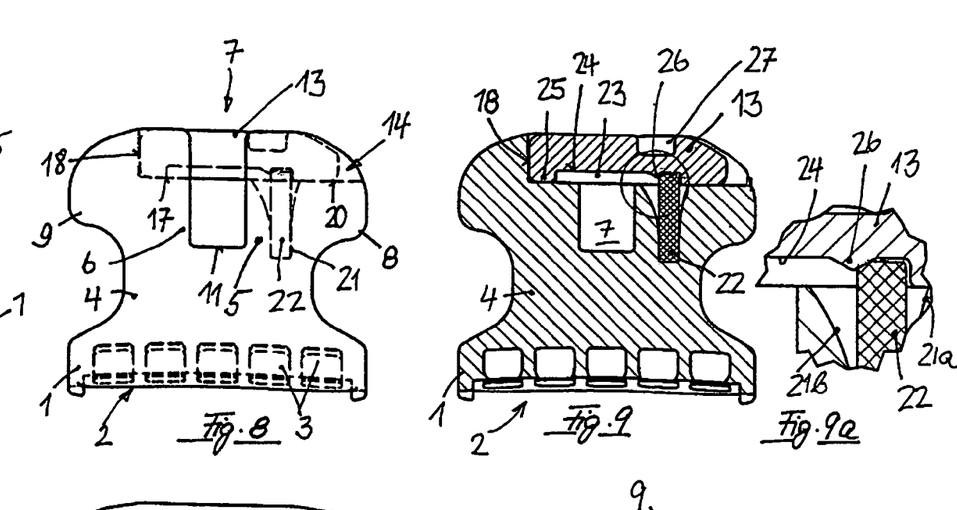
Figure 10:
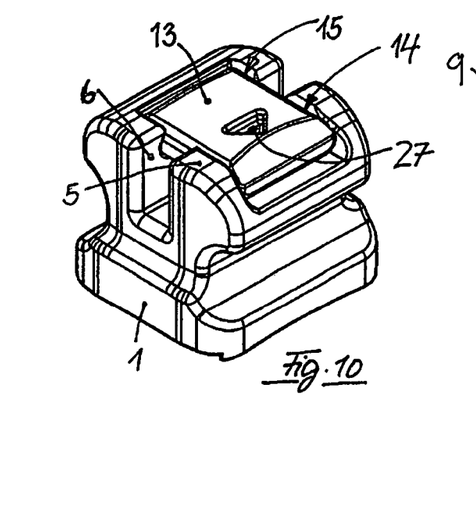

The arrangement of the projection 26 is such that in the closed position of the slide 13 it comes to lie on the side of the spring 22 that faces the slot 7, in contact with the spring 22—see FIG. 9 and FIG. 9a. Preferably, the position of the projection 26 is selected to ensure that in the closed position of the slide 13 the restoring force of the spring will have been substantially exhausted so that the spring 22 will be substantially free from any forces in that position. During transfer of the slide 13 to its closed position, the spring 22 can be easily overcome by the projection 26, the projection 26 deflecting the spring 22 in the direction of the surface 21b. Once the spring 22 has been overcome by the vertex of the projection 26, the spring is restored to its substantially straight shape by the restoring force that had built up before. When the slide 13 is to be transferred to its open position, the spring 22 cannot be deflected to the same degree as during the closing process because the surface 21a is closer to the spring 22 than the surface 21b. However, the projection 26 is still capable of overcoming the spring 22 because its height, measured from the base 24 of the recess 23, is smaller than the depth of the recess 23 at the bottom of the slide 13. The resistance that has to be overcome during that process is sufficiently high to retain the slide 13 in its closed position at the forces typically encountered in a person's mouth. In order to be able to apply the force required for opening the bracket, an indentation 27 is provided in the upper surface of the slide 13 that can be engaged by a tool, for example a scaler, for displacement of the slide 13.

The embodiment illustrated in FIGS. 13 to 24 differs from that illustrated in FIGS. 1 to 12 in that a spring 22 and 24, respectively, in the form of a leaf spring is provided not only in the gingival wall 5, but also in the occlusal wall 6 of the bracket. Preferably, the two springs 22 and 28 have the same configuration and extend in parallel to the slot 7. Each of them projects beyond the base 17 or 20, respectively, of the recess 14 or 15, respectively, and both of them are beveled with their beveled surface 29 facing away from the second stop 18. Alternatively, the two springs 22 and 28 may, however, project beyond the base 17 or 10 of the recess 14 or 15, respectively, a different length in which case differently high forces would be required for the slide 13 to overcome the springs 22 and 28. Contrary to the first embodiment, the slot-shaped recess 21 provided in the gingival wall 5 is expanded to one side only and is provided with a curved surface area 21b only in the neighborhood of the slot 7. The other curved surface 21a of the first embodiment has been omitted.

The other spring 28 is seated in a slot-shaped recess 30, the upper portion of which is provided with, and expanded by, two curved surface portions 30a and 30b provided in symmetrical arrangement.

The projection 26 present in the first embodiment has been omitted. Consequently, there only exists a flat cuboid recess 23 at the bottom of the slide 13.

When the slide 13 is introduced into the guide 14 to 17 of the bracket for the first time, its forward end 19 hits upon the beveled surface 29 of the first spring 22 thereby bending the latter toward the curved surface 21b until the slide 13 is in a position to slide over the projecting end of the spring 22, which operation is facilitated by the beveled surface 29 and a rounded lower edge at the forward end 19 of the slide 13. The slide 13 is then secured on the bracket as, instead of hitting upon the inclined surface 29 of the spring 22, the stop 25 of the bracket hits upon that side of the spring that faces the slot 7 and that extends in parallel to the stop 25. As the slot-shaped recess 21 is not expanded on the side of the spring 22 facing the slot 7, the projecting end of the spring 22 cannot give way when a pulling force is exerted on the slide 13 so that the spring 22 can no longer be overcome by the slide 13. For transferring the slide 13 from its open position (FIG. 15) to its closed position (FIG. 21), the slide 13 is moved against the stop 18, thereby overcoming the second spring 28 by its stop 25 in the same way in which it has overcome the spring 22 before. However, the slide 13 can be returned from its closed position to its open position because the second spring 28 can be deflected in both directions so that the slide 13, once having overcome a resistance which, desirably, is higher during opening than during closing of the bracket, can be transferred back to its open position.

LIST OF REFERENCE NUMERALS

1 Base
2 Bottom
3 Indentations
4 Base

5 Gingival wall
6 Occlusal wall
7 Groove, slot
8 Gingival ligature wing
9 Occlusal ligature wing
10 Arch wire
11 Base of 7
12 Edges of 7
13 Slide
14 Labial recess in 5
15 Labial recess in 6
16 Undercuts
17 Base of 15
18 Second stop
19 Front end of 13
20 Base of 14
21 (Slot-shaped) recess in 5
21a Surface of 21
21b Surface of 21
22 Spring, first spring
23 Recess in the bottom of 13
24 Base of 23
25 Stop, first stop
26 Projection on 24
27 Indentation
28 Second spring
29 Beveled surface on 22 and 28
30 Slot-shaped recess in 6
30a Curved surface portion
30b Curved surface portion

What is claimed is:

1. A self-ligating bracket for use in orthodontics comprising a base;
an occlusal wall extending from the base and having at least one occlusal ligature wing;
a gingival wall extending from the base and having at least one gingival ligature wing;
a slot separating the occlusal wall and the gingival wall from one another and extending continuously in the mesial-to-distal direction;
a slide retained in a guide provided in one or both of the occlusal wall and the gingival wall and arranged for displacement in the guide in a gingival-to-occlusal direction, between a closed position, in which the slide bridges the slot, and an open position in which the slot is open in a labial direction;
a leaf spring for retaining of the slide in both the closed position and the open position;
a spring recess for seating the leaf spring, the spring recess being arranged in one of the gingival wall and the occlusal wall of the bracket and provided with an opening facing the slide, a spring end projecting toward an outside of the spring recess;
a first stop on the slide abutting against the spring end in the open position of the slide;
a projection on the slide, facing the spring end, and arranged in order that during displacement of the slide to the closed position, the projection abuts the spring end before it reaches the closed position, sufficient space being available on both sides of the projection for accommodating the spring end projecting from the spring recess;
the spring recess for the leaf spring expanding toward a spring recess opening facing the slide so that the leaf spring has sufficient play, in the recess, for bending the spring leaf in two possible directions of displacement of the slide the spring recess opening being nonsymmetrical and having surfaces displaced from the leaf spring end at different distances for causing greater resistance to open the slide than to close the slide; and
a second stop on the bracket, for abutment of the slide in the closed position, once the projection has overcome the spring.

2. The bracket as defined in claim 1 wherein the leaf spring is seated in the gingival wall of the bracket and the second stop is formed on the occlusal wall of the bracket.

3. The bracket as defined in claim 1 wherein a forward end of the slide abuts the second stop.

4. The bracket as defined in claim 1 wherein the leaf spring is provided in the gingival wall and the second stop is provided on the occlusal wall.

5. The bracket as defined in claim 1, wherein the opening of the recess faces away from the base.

6. The bracket as defined in claim 1, wherein the recess extends at approximately a right angle relative to the slide.

7. The bracket as defined in claim 1, wherein the first stop is flat on a side facing the leaf spring in the closed position, and is rounded on a side facing away from a corresponding spring.

8. The bracket as defined in claim 1, wherein the projection has a wedge-shaped configuration.

9. The bracket as defined in claim 1, wherein the outer edges of the slide, which face the base of the slot in the closed position of the slide, are rounded.

10. A self-ligating bracket for use in orthodontics comprising:
a base;
an occlusal wall extending from the base and having at least one occlusal ligature wing;
a gingival wall extending from the base and having at least one gingival ligature wing;
a slot separating the occlusal wall and the gingival wall from one another and extending continuously in the mesial-to-distal direction;
a slide retained in a guide provided in one or both of the occlusal wall and the gingival wall and arranged for displacement in the guide in a gingival-to-occlusal direction, between a closed position, in which the slide bridges the slot, and an open position in which the slot is open in a labial direction;
at least one first leaf spring and at least one second leaf spring, each seated in a respective recess, each respective recess provided with an opening facing the slide, with respective spring ends projecting from the respective openings for retaining the slide in both the closed position and the open position, the recess for the at least one first leaf spring being provided in a first wall of a bracket, the recess for the second leaf spring being provided in a second wall of the bracket;
a first stop on the slide abutting the first leaf spring in the open position of the slide and abutting the second leaf spring in the closed position of the slide;
the first spring recess enabling the first leaf spring to expand toward the first spring recess opening so that the first leaf spring is has play within the first spring recess for enabling bending of the first leaf spring in a closing direction of the slide, the first spring recess opening being nonsymmetrical and having surfaces displaced from the first leaf spring end at different distances for causing greater resistance to open the slide than to close the slide;
the second spring recess enabling the second leaf spring to expand toward the second spring recess opening so that the second leaf spring is given sufficient play within the second spring recess for enabling bending of the second leaf spring in two possible directions of displacement of the slide;

a first space available in first spring recess being configured and sized that, when introduced into the guide for a first time, the slide will urge the first leaf spring into an expanded portion of the respective recess, by bending of the first leaf spring, until the first stop of the slide is capable of overcoming the first leaf spring;

a second space available in the second spring recess for bending of the respective second leaf spring, the second leaf spring being configured and sized that the first stop of the slide is capable of overcoming the second leaf spring in both possible directions of displacement by bending of the second spring, the second spring recess opening being nonsymmetrical and having surfaces displaced from the second leaf spring end at different disclosures for causing greater resistance to open the slide than to close the slide; and and a second stop on the bracket, abutting the slide wall in a closed position once it has overcome the second spring.

11. The bracket as defined in claim 10, wherein the first leaf spring is seated in the first wall of the bracket and that the second stop for the slide is formed on the second wall of the bracket.

12. The bracket as defined in claim 10 wherein the first wall is the gingival wall and the second wall is the occlusal wall of the bracket.

13. The bracket as defined in claim 1 or claim 10, wherein the slide is a predominantly flat structure.

14. The bracket as defined in claim 10, wherein the leaf springs are seated in the respective recesses loosely, or are retained by friction.

15. The bracket as defined in claim 10, wherein at least a part of the springs is made from metal.

16. The bracket as defined in claim 10, wherein at least a part of the leaf springs is made from a plastic material with an elastic or elastomeric modulus of elasticity.

17. The bracket as defined in claim 16, wherein the plastic material is a polyoximethylene (POM).

18. The bracket as defined in claim 1 or claim 10, wherein the bracket is formed of a ceramic material.

19. The bracket as defined in claim 18, wherein the bracket is formed of aluminum oxide.

20. The bracket as defined in claim 18, wherein a bracket body consists of aluminum oxide wherein the slide consists of a ceramic material having a strength higher than aluminum oxide.

21. The bracket as defined in claim 10, wherein the first and second leaf springs are beveled at respective projecting ends in a manner such that the beveled surfaces point to corresponding opening directions of the slide.

22. The bracket as defined in claim 1 or claim 10, wherein outer edges of the slot are rounded.

23. The bracket as defined in claim 10, wherein the first spring end projects a greater distance from the first spring recess than the second spring end project from the second spring recess.

* * * * *